United States Patent [19]

Loney et al.

[11] Patent Number: 5,417,658
[45] Date of Patent: May 23, 1995

[54] BALLOON DILATATION CATHETER HAVING A TORSIONALLY SOFT COMPONENT

[75] Inventors: Carol Loney, St. Louis Park; David A. VandenEinde, Minneapolis, both of Minn.

[73] Assignee: SciMed Life Systems, Inc., Maple Grove, Minn.

[21] Appl. No.: 257,475

[22] Filed: Jun. 9, 1994

Related U.S. Application Data

[63] Continuation of Ser. No. 126,102, Sep. 23, 1993, abandoned, which is a continuation of Ser. No. 852,547, Mar. 17, 1992, abandoned.

[51] Int. Cl.⁶ .................................................. A61M 29/00
[52] U.S. Cl. ........................................ 604/96; 606/194
[58] Field of Search .................. 604/96, 95, 101–104, 604/280, 283; 606/192, 194

[56] References Cited

U.S. PATENT DOCUMENTS

| | | |
|---|---|---|
| 3,402,717 | 9/1968 | Doherty . |
| 3,837,347 | 9/1974 | Tower . |
| 4,261,339 | 4/1981 | Hanson et al. . |
| 4,413,989 | 11/1983 | Schjeldahl et al. . |
| 4,606,347 | 8/1986 | Fogarty et al. . |
| 4,616,653 | 10/1986 | Samson et al. . |
| 4,715,378 | 12/1987 | Pope, Jr. et al. . |
| 4,771,778 | 9/1988 | Mar . |
| 4,793,350 | 12/1988 | Mar et al. . |
| 4,813,934 | 3/1989 | Engelson et al. . |
| 4,821,722 | 4/1989 | Miller et al. . |
| 4,838,268 | 6/1989 | Keith et al. . |
| 4,846,174 | 7/1989 | Willard et al. . |
| 4,848,344 | 7/1989 | Sos et al. . |
| 4,917,088 | 4/1990 | Crittenden . |
| 4,943,278 | 7/1990 | Euteneuer et al. . |
| 4,964,409 | 10/1990 | Tremulis . |
| 4,976,720 | 12/1990 | Machold et al. . |
| 4,998,917 | 3/1991 | Gaiser et al. . |
| 4,998,923 | 3/1991 | Samson et al. ............ 604/95 X |
| 5,002,559 | 3/1991 | Tower . |
| 5,003,989 | 4/1991 | Taylor et al. . |
| 5,032,113 | 7/1991 | Burns . |
| 5,042,985 | 8/1991 | Elliott et al. . |
| 5,055,109 | 10/1991 | Gould et al. ............... 606/194 |
| 5,059,176 | 10/1991 | Winters . |
| 5,102,390 | 4/1992 | Crittenden et al. . |
| 5,104,376 | 4/1992 | Crittenden ................. 604/96 |
| 5,135,487 | 8/1992 | Morrill et al. . |
| 5,135,494 | 8/1992 | Engelson et al. . |
| 5,141,518 | 8/1992 | Hess et al. . |
| 5,156,595 | 10/1992 | Adams . |
| 5,171,221 | 12/1992 | Samson . |
| 5,195,989 | 3/1993 | Euteneuer . |
| 5,209,728 | 5/1993 | Kraus et al. . |
| 5,246,420 | 9/1993 | Kraus et al. ............... 604/95 |
| 5,256,144 | 10/1993 | Kraus et al. ............... 604/96 |
| 5,279,561 | 1/1994 | Roucher et al. . |
| 5,318,529 | 6/1994 | Kontos ....................... 604/96 |
| 5,324,259 | 6/1994 | Taylor et al. ............... 604/96 |
| 5,324,263 | 6/1994 | Kraus et al. ............... 604/96 |

FOREIGN PATENT DOCUMENTS

| | | |
|---|---|---|
| 0368523 | 10/1989 | European Pat. Off. . |
| 0462801 | 6/1991 | European Pat. Off. . |
| WO91/00136 | 9/1991 | WIPO . |
| WO92/08511 | 5/1992 | WIPO . |

*Primary Examiner*—John D. Yasko
*Attorney, Agent, or Firm*—Nawrocki, Rooney & Sivertson

[57] ABSTRACT

A non-over-the-wire catheter for use in angioplasty including a core wire which extends distally beyond a distal end of a tubular member. The tubular member defines an interior passage which is in fluid communication with a distal interior passage of a waist tube that extends about the core wire. An inflatable balloon member extends about the core wire and is in fluid communication with the distal interior passage of the waist tube. A torsionally soft component is coupled between the balloon member and the core wire. The torsionally soft component absorbs torque applied to the tubular member and conveyed along the core wire such that the torque is not readily transmitted to the balloon member from the core wire.

23 Claims, 3 Drawing Sheets

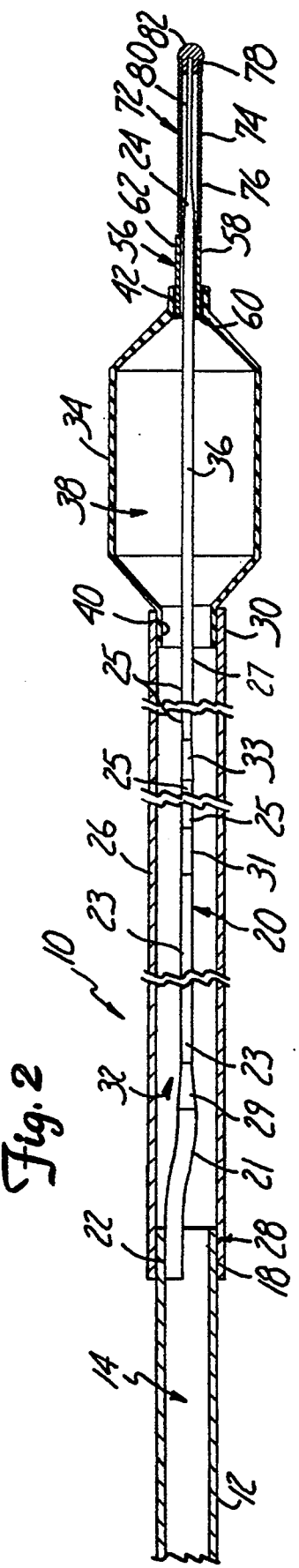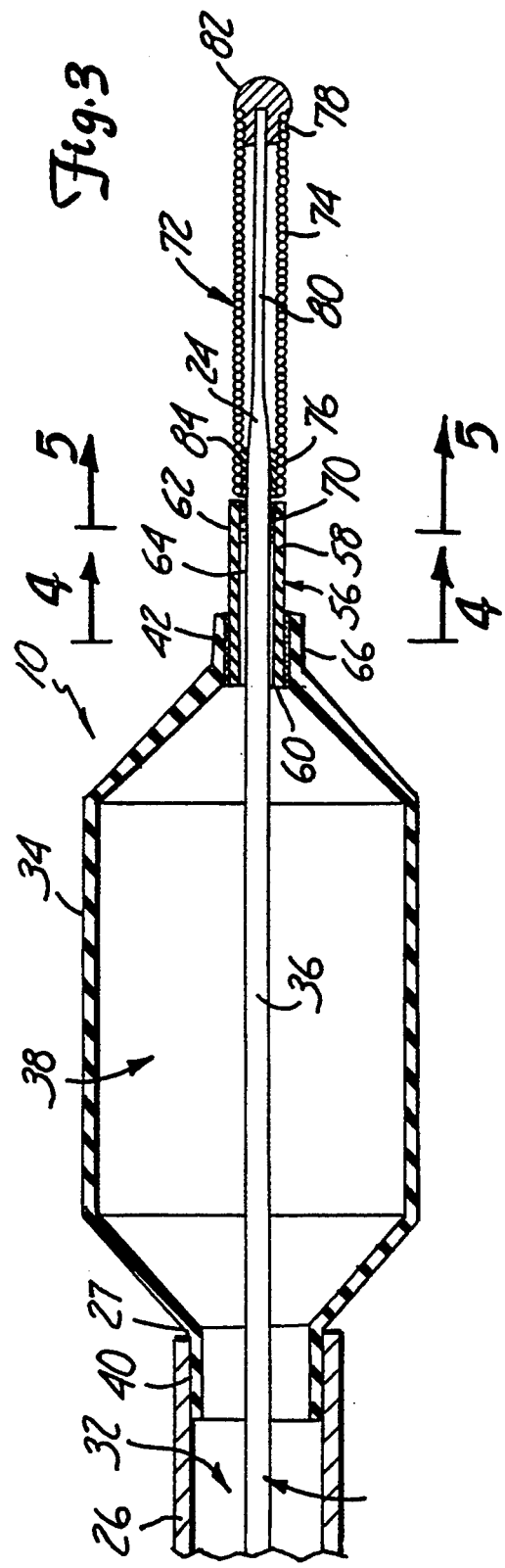

BALLOON DILATATION CATHETER HAVING A TORSIONALLY SOFT COMPONENT

This application is a continuation of Ser. No. 08/126,102 filed Sep. 23, 1993 now abandoned which is a continuation of Ser. No. 07/852,547 filed Mar. 17, 1992 now abandoned.

REFERENCE TO COPENDING APPLICATIONS

Reference is made to the following commonly assigned applications which were filed on even date with this application and are entitled as follows:

(1) Balloon Dilatation Catheter Having A Free Core Wire (Ser. No. 07/852,545); and (2) Balloon Dilatation Catheter Having Dual Sealing Plugs (Ser. No. 07/852,546).

BACKGROUND OF THE INVENTION

The present invention relates to the field of percutaneous transluminal coronary angioplasty (PTCA). In particular, the present invention is a non-over-the-wire dilatation balloon catheter.

Angioplasty has gained wide acceptance in recent years as an efficient and effective method for treating certain types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Typically, the catheter is introduced and directed partially through a patient's vascular system via a guide catheter. Using fluoroscopy, a physician guides the catheter through that portion of the patient's vascular system distal of the guide catheter until the balloon is positioned across the stenosis. While the catheter is being steered through the vascular system, the balloon is in a deflated state, wrapped (i.e., folded) tightly about the distal end of the catheter to reduce the profile of the balloon. Reducing the profile of the balloon allows the catheter to easily travel through the guide lumen of the guide catheter and traverse arterial vessels and stenoses having small through openings. Once the catheter is positioned with the balloon across the stenosis, the balloon is inflated by supplying fluid under pressure through an inflation lumen to the balloon. Inflation of the balloon causes stretching of the artery and pressing of the lesion into the artery wall to re-establish an acceptable blood flow through the artery.

Over-the-wire catheters and non-over-the-wire catheters are two types of dilatation catheters that are commonly used in angioplasty. An over-the-wire catheter has an inflation lumen and a guide wire lumen through which a separate guide wire is advanced to establish a path to the stenosis. Since the guide wire is separate from the catheter, torque applied to the guide wire to steer the guide wire through the vascular system and across the stenosis is not conveyed to any part of the catheter. Once a distal end of the guide wire is across the stenosis, the separate over-the-wire catheter is advanced over the guide wire until the balloon is positioned across the lesion.

One type of non-over-the-wire catheter has its own built in guide wire (sometimes referred to as a core wire) which is joined to a hypotube, such that the core wire, balloon and inflation lumen comprise a single unit. Due to this single unit construction, torque (i.e., a rotational force) applied to a proximal end of a hypotube of the non-over-the-wire catheter (to which the core wire is fixedly attached) to steer the catheter through the vascular system and across the stenosis, is conveyed to other parts of the catheter.

In particular, torque induced rotation applied to the hypotube and core wire combination is transmitted to a distal end of the balloon and to a proximal end of a waist tube that extends about the core wire and couples the hypotube to the balloon. However, due to the tortuosity of portions of the guide catheter and of the patient's vascular system, the balloon and the waist tube may contact parts of the walls of the guide catheter guide lumen and the arterial vessels. This contact may cause rotation of portions of the balloon and the waist tube to lag behind rotation of the hypotube and core wire combination. The lag in balloon rotation dampens steering responsiveness of the balloon catheter itself, since contact of the balloon with the walls of the guide lumen and arterial vessels imparts drag to the distal end of the core wire. This, in turn, dampens the responsiveness of the core wire distal spring tip.

Typically, a spring tip is provided at the distal end of the core wire and is formed with a J-bend. The J-bend permits the balloon catheter to be steered into desired arterial branches. That is, torque induced rotation applied to the hypotube is transmitted to the spring tip through the core wire to position the J-bend to enter the desired arterial branch. A non-uniform ability to accurately position the J-bend of the spring tip, such as may be caused by a lag in balloon rotation which dampens steering responsiveness, makes the balloon catheter difficult to steer and may unnecessarily prolong the angioplasty procedure.

In addition, the lag in balloon rotation causes the balloon and the waist tube to twist upon themselves. The balloon tends to twist upon itself proximally from its distal attachment to the core wire, while the waist tube twists upon itself distally from its proximal attachment to the hypotube. If balloon twist is minimal, as a result of minimal steering torque applied to the hypotube, the balloon will untwist upon application of inflation fluid pressure to inflate the balloon once the balloon is positioned across a stenosis. However, if balloon twist is significant, the balloon may not inflate uniformly. Non-uniform balloon inflation exhibits balloon behavior wherein portions of the balloon (i.e., constrictions in the balloon due to twist) do not inflate to their maximum diameter. These under-inflated constrictions do not uniformly press the stenosis into the arterial wall and hence, do not effectively dilate the lesion to allow acceptable blood flow through the arterial vessel. In addition, upon deflation of the balloon, those segments of the balloon (i.e., segments adjacent the constrictions) which were fully inflated may not completely deflate. These partially deflated segments may make withdrawal of the balloon catheter from the patient's vascular system back through the guide catheter difficult.

It is desirable in a non-over-the-wire catheter to reduce the transmission of torque (applied to the hypotube and core wire combination) to the balloon of the catheter. The reduction in torque transmission would abate twisting of the balloon as the catheter is steered through the vascular system, and thereby permit uniform inflation and deflation of the balloon which is needed to effectively dilate the stenosis to re-establish an acceptable blood flow through the arterial vessel. In addition, the reduction in torque transmission, from the core wire to the balloon, would reduce, if not eliminate, the twisting of the balloon from the lag in balloon rotation upon the application of torque to the core wire. This reduction in balloon twist would alleviate steering difficulties sometimes associated with non-over-the-wire catheters wherein torque is readily transmitted from the core wire to the balloon.

SUMMARY OF THE INVENTION

The present invention is a catheter for use in angioplasty. The catheter includes an elongate flexible tubular member having an interior passage extending from a proximal end to a distal end. A guiding member having proximal and distal ends is secured at its proximal end to the tubular member adjacent its distal end, so that the guiding member extends distally beyond the distal end of the tubular member. An elongate flexible waist tube having proximal and distal ends is sealably connected at its proximal end to the tubular member adjacent its distal end, such that the waist tube extends distally beyond the distal end of the tubular member about the guiding member to define a distal interior passage in fluid communication with the interior passage of the tubular member. An inflatable balloon member extends around a section of the guiding member and has an interior in fluid communication with the distal interior passage of the waist tube. The balloon member includes a proximal end sealably connected to the distal end of the waist tube and a distal end that extends coaxially about a portion of the guiding member. A torsionally soft component couples the balloon member to the guiding member. The torsionally soft component absorbs torque which is applied to the proximal end of the tubular member and is conveyed along the guiding member, such that the torque is not readily transmitted to the balloon member from the guiding member.

In one embodiment, the torsionally soft component is a torsionally flexible tubular element having a proximal end, a distal end and a through opening that extends between the proximal and distal ends and is adapted to receive the guiding member therethrough. The proximal end of the tubular element is secured to the distal end of the balloon member and the distal end of the tubular element is secured to the guiding member, such that the tubular element extends distally beyond the distal end of the balloon member.

In an alternative embodiment, the catheter includes a substantially rigid inner sleeve that has a proximal end, a distal end and a through lumen that extends between the proximal and distal ends. The through lumen is configured to freely receive the guiding member, such that the guiding member can rotate relative to the inner sleeve upon the application of torque to the proximal end of the tubular member. The inner sleeve extends proximally from the distal end of the balloon member. In this embodiment, the tubular element that defines the torsionally soft component is secured at its distal end to the proximal end of the inner sleeve and at its proximal end to the guiding member, such that the tubular element extends proximally from the proximal end of the inner sleeve. In both embodiments, the catheter includes a radiopaque spring tip positioned distally of the distal end of the balloon member.

The non-over-the-wire catheter of the present invention is relatively uncomplicated and since the distal end of the balloon member is coupled to the guiding member via the torsionally soft component, the guiding member can be rotated relative to the balloon member with minimal twisting of the balloon member as the catheter is steered through the vascular system of a patient. This reduction in balloon twist permits uniform inflation and deflation of the balloon which is needed to effectively dilate the stenosis and reestablish acceptable blood flow through the arterial vessel.

Moreover, the non-transmission of torque from the guiding member to the balloon member reduces, if not eliminates balloon rotation. Hence, the effects (i.e, dampened steering responsiveness) due to the lag in balloon rotation upon application of torque to the guiding member are substantially decreased. The effects of balloon rotation lag are decreased and steering responsiveness improved, because contact between the balloon and the interior wall of a guide catheter and the walls of arterial vessels no longer imparts drag to the distal end of the guiding member. This lack of drag alleviates steering difficulties sometimes associated with non-over-the-wire catheters wherein torque is readily transmitted from the guiding member to the balloon.

In addition, the torsionally soft component prevents the balloon member and waist tube from being displaced proximally or distally along the guiding member as the catheter is being maneuvered through a vascular system of a patient.

BRIEF DESCRIPTION OF THE DRAWINGS

FIG. 2 is an enlarged sectional view of a distal end of the balloon catheter shown in FIG. 1.

FIG. 3 is a greatly enlarged sectional view similar to FIG. 2 showing details of the distal end of the first preferred embodiment of the balloon catheter.

DETAILED DESCRIPTION OF THE PREFERRED EMBODIMENTS

Figure 1:
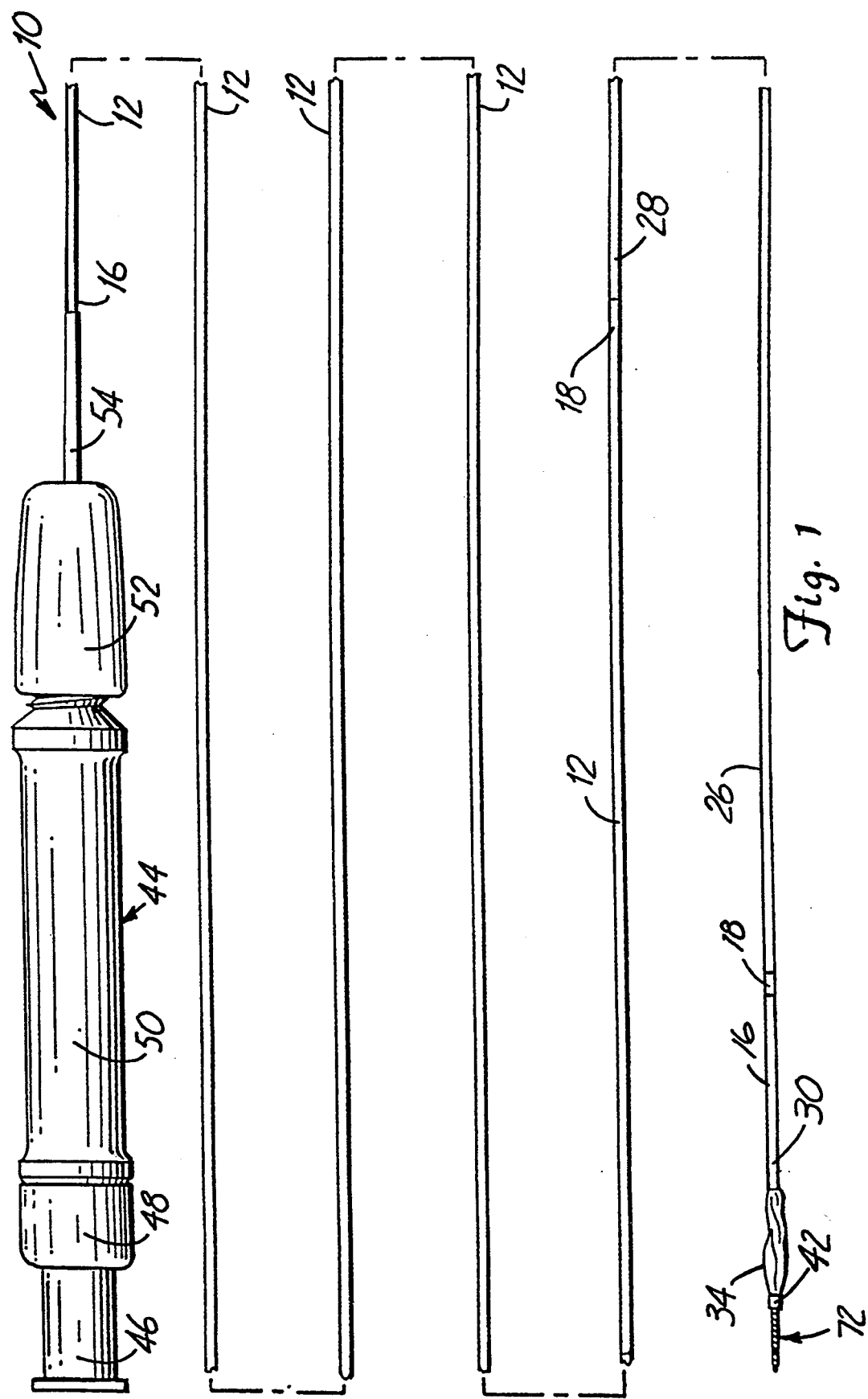
FIG. 1 is an elevational view of a first preferred embodiment of a balloon catheter in accordance with the present invention.

A non-over-the-wire catheter 10 in accordance with the present invention is illustrated generally in FIG. 1. The catheter 10 includes an elongate flexible tubular member (i.e., hypotube) 12 having an interior passage 14 (See FIG. 2) extending from a proximal end 16 to a distal end 18. As seen best in FIG. 2, a core wire 20 has a proximal end 22 and a distal end 24. The proximal end 22 of the core wire 20 is joined to the tubular member 12 adjacent to its distal end 18, with the core wire 20 extending distally beyond the distal end 18 of the tubular member 12.

The core wire 20 preferably provides varying flexibility along its length such that its flexibility increases in the distal direction. As illustrated in FIG. 2 (not shown to scale), this may be accomplished by having a core wire with one or more ground tapers. In one embodiment, the tubular member 12 is preferably formed from Type 304 stainless steel hypodermic tubing, and the core wire 20 is preferably formed from Type 304 stainless steel and manufactured by centerless grinding. The core wire 20 preferably has four main sections 21, 23, 25 and 27 and three tapered sections 29, 31 and 33. The core wire 20 is preferably stress relieved by exposing the wires before grinding to a temperature in a range of from 500° F. to 800° F. for a time period from about 30 min. to about 6 hours, and preferably at 750° F. for about 5 hours including ramp-up time. Preferably, the first section 21 is approximately 1.25 in. long and has a diameter of approximately 0.012 in. The second section 23 is approximately 4 in. long and has a diameter of approximately 0.0095 in. The third section 25 is approximately 3 in. long and has a diameter of approximately 0.0075 in. The fourth section 27 is approximately 2.5 in. long and has a diameter of approximately 0.0053 in. The first, second and third tapered sections 29, 31 and 33, respectively, are each approximately 1 in. in length.

The core wire 20 is preferably joined to the tubular member 12 by a braze material composed of a silver brazing metal powder with a brazing flux such as (BAg-7-325 mesh) available from Turbo-Braze, Corp. (Union, N.J.). Alternatively, the core wire 20 can be joined to the tubular member 12 by a silver solder material composed of 4% silver and 96% tin.

Other materials, such as a super elastic alloy (otherwise known as a shape memory alloy) may be used for the tubular member 12. For example, TINEL available from Raychem, Corp. (Menlo Park, Calif.) or a Nickel-Titanium shape memory alloy available from Shape Memory Applications, Inc. (Sunnyvale, Calif.). An adhesive material, such as cyanoacrylate, may be used to join a core wire 20 to a tubular member 12 composed of a super elastic alloy.

The catheter 10 further includes an elongate flexible waist tube 26 having a proximal end 28 and a distal end 30. The proximal end 28 of the waist tube 26 is sealably connected to the tubular member 12 adjacent its distal end 18. As seen best in FIG. 2, the waist tube 26 extends distally beyond the distal end 18 of the tubular member 12 and about the core wire 20 to define a distal interior passage 32. The distal interior passage 32 is in fluid communication with the interior passage 14 of the tubular member 12.

As seen in FIG. 2, an inflatable balloon member 34 extends about a section 36 of the core wire 20. The balloon member 34 has an interior 38 in fluid communication with the distal interior passage 32 of the waist tube 26. The balloon member 34 further includes a proximal end 40 and a distal end 42. The proximal end 40 of the balloon member 34 is sealably connected to the distal end 30 of the waist tube 26. The distal end 42 of the balloon member 34 extends coaxially about the core wire 20.

In one embodiment, the waist tube 26 is preferably formed of a polymer material, such as polyethelene. For example, PETROTHENE (HD, LB5003, HDPE) available from Quantum, USI Division (Cincinnati, Ohio). The balloon member 34 is preferably formed of a polymer material such as polyolefin which has been treated by radiation cross linking. The balloon member 34 may also be silicone coated. A suitable polyolefin is available from E.I. DuPont Nemours & Co. (Wilmington, Del.) under the tradename SURYLYN ® (8527 POC) Ionomer. The waist tube 26 is preferably bonded to the tubular member 12 and to the balloon member 34 by a suitable adhesive and sealing material. For example, LOCTITE PRISM 405, a cyanoacrylate, available from Loctite, Corp. (Newington, Conn.) or TRA-BOND 2135D, an epoxy, available from Tra-Con, Inc. (Medford, Mass.).

As seen in FIG. 1, a manifold fitting 44 is mounted on the proximal end 16 of the tubular member 12 to facilitate connection with an inflation device (not shown) for the introduction and removal of pressurized balloon fluid to the catheter 10 to inflate and deflate the balloon member 34 via interior passage 14 and distal interior passage 32. The manifold fitting 44 includes a luer fitting 46 (for connection to the inflation device), a first end cap 48, a manifold body 50, a second end cap 52 and a strain relief tube 54.

Figure 5:
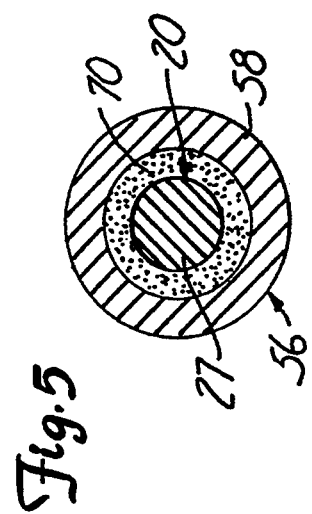
FIG. 5 is a greatly enlarged cross sectional view taken along line 5—5 of FIG. 3.
Figure 4:
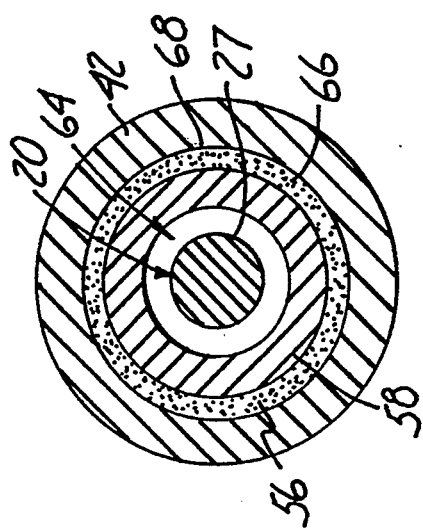
FIG. 4 is a greatly enlarged cross sectional view taken along line 4—4 of FIG. 3.

In the preferred embodiment shown in FIGS. 2 and 3, the catheter 10 further includes a torsionally soft component 56 defined by a torsionally flexible tubular element 58 having a proximal end 60 and a distal end 62. A through opening 64 extends between the proximal end 60 and the distal end 62 of the tubular element 58. The proximal end 60 of the tubular element 58 is preferably secured to an inner circumferential surface 66 of the distal end 42 of the balloon member 34 by a suitable adhesive and sealing material 68, such as TRA-BOND 2135D, an epoxy, available from Tra-Con, Inc. (Medford, Mass.) (see FIG. 4). The core wire 20 extends through the through opening 64 of the tubular element 58, and the distal end 62 of the tubular element 58 is secured to the core wire 20 adjacent its distal end 24. The tubular element 58 is sealed and secured to the core wire 20 by an adhesive and sealing material 70, such as TRA-BOND 2135D, an epoxy, available from Tra-Con, Inc. (Medford, Mass.) (see FIG. 5).

The tubular element 58 that defines the torsionally soft component 56 is preferably formed from a torsionally soft material such as PELLETHANE available from Dow Chemical Co. (Midland, Mich.). The tubular element 58 absorbs torque which is applied to the proximal end 16 of the tubular member 12 (such as may be applied to steer the catheter 10 through the vascular system of a patient to position the balloon member 34 across a stenosis) and is conveyed along the core wire 20, such that the torque is not readily transmitted to the balloon member 34 from the core wire 20. The tubular element 58 is formed of material that has greater torsional flexibility than the material of the balloon member 34 and the waist tube 26. Therefore, torque from the core wire 20 twists the tubular element 58 thereby resulting in minimal twisting of the balloon member 34 and the waist tube 26. This translates into increased steering responsiveness of the catheter 10, since balloon rotation is virtually eliminated, along with the effects of balloon rotation lag.

As seen in FIG. 3, the catheter 10 further includes a radiopaque spring tip 72 positioned distally of the distal end 62 of the tubular element 58. The spring tip 72 includes a flexible, helical coil member 74 having a proximal end 76 and a distal end 78. The helical coil member 74 is preferably formed from radiopaque platinum alloy wire composed of 90% Pt and 10% Ir. The spring tip 72 is preferably 25 mm in length with varying flexibility. Alternatively, the spring tip 72 may be 15 mm in length with varying flexibility. A shaping ribbon 80 is integral with the core wire 20. A first joint 82, preferably comprising a weld, connects the distal end 78 of the coil member 74 to the shaping ribbon 80. A second joint 84 couples the proximal end 76 of the coil member 74 to the distal end 24 of the core wire 20. The second joint 84 preferably comprises a solder joint consisting of a silver solder material composed of 4% silver and 96% tin. Alternatively, the second joint 84 may comprise a braze joint consisting of a braze material composed of a silver brazing metal powder with a brazing flux such as (BAg-7-325 mesh) available from Turbo-Braze, Corp. (Union, N.J.).

Figure 6:
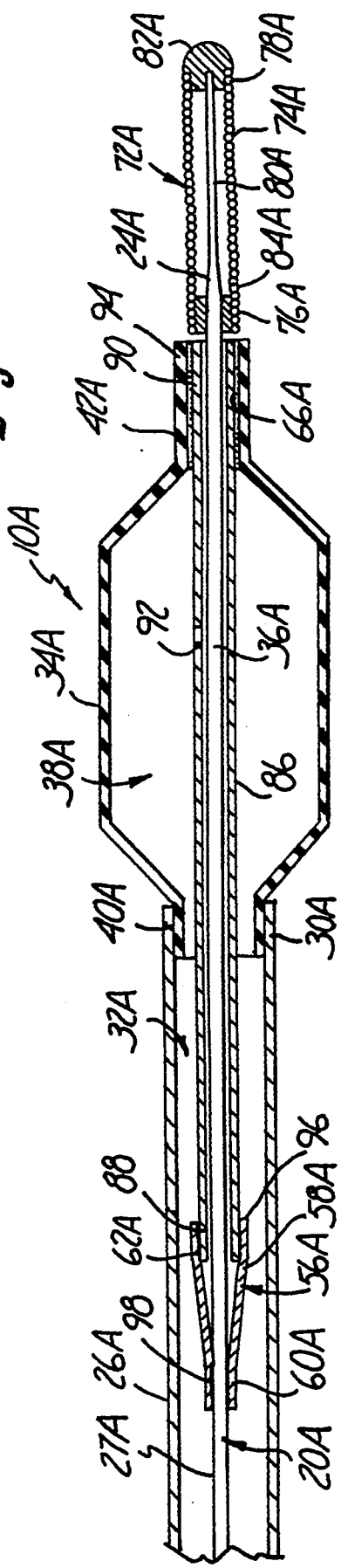
FIG. 6 is a greatly enlarged sectional view showing details of an alternative embodiment of a distal end of the balloon catheter in accordance with the present invention.

In an alternative embodiment illustrated in FIG. 6, the catheter 10A includes a substantially rigid inner sleeve 86. The inner sleeve 86 includes a proximal end 88, a distal end 90 and a through lumen 92 that extends between the proximal and distal ends 88 and 90. The through lumen 92 of the inner sleeve 86 is configured to freely receive the modified core wire 20A, such that the core wire 20A can rotate relative to the inner sleeve 86 upon the application of torque to the proximal end of the tubular member.

The distal end 90 of the inner sleeve 86 is preferably sealed and secured to the inner circumferential surface 66A of the distal end 42A of the balloon member 34A by a suitable adhesive and sealing material 94, such as TRA-BOND 2135D, an epoxy, available from Tra-Con, Inc. (Medford, Mass.). The inner sleeve 86 extends proximally along the core wire 20A from the distal end 42A of the balloon member 34A. The distal end 62A of the tubular element 58A, that defines the torsionally soft component 56A, is preferably sealed and secured to the outer surface of the proximal end 88 of the inner sleeve 86 by a suitable adhesive and sealing material 96, such as TRA-BOND 2135D, an epoxy, available from Tra-Con, Inc. (Medford, Mass.). The proximal end 60A of the tubular element 58A is secured to the core wire 20A, such that the tubular element 58A extends proximally from the proximal end 88 of the inner sleeve 86. The tubular element 58A is preferably sealed and secured to the core wire 20A by a suitable adhesive and sealing material 98, such as TRA-BOND 2135D, an epoxy, available from Tra-Con, Inc. (Medford, Mass.).

The inner sleeve 86 is preferably formed from a polyimide, such as is available from HV Technologies, Inc. (Trenton, Ga.). Alternatively, the inner sleeve 86 may be formed from a polyethylene terephthalate (PET). Like the first embodiment, the tubular element 58A is formed of material that has greater torsional flexibility than the material of the balloon member 34A, the waist tube 26A and the inner sleeve 86. Therefore, the tubular element 58A absorbs torque which is applied to the proximal end of the tubular member (such as may be applied to steer the catheter 10A through the vascular system of a patient to position the balloon member 34A across a stenosis) and is conveyed along the core wire 20, such that the torque is not readily transmitted to the balloon member 34 through the inner sleeve 86 from the core wire 20. Torque from the core wire 20A twists the tubular element 58A thereby resulting in minimal twisting of the balloon member 34A, the waist tube 26 and the inner sleeve 86. This translates into increased steering responsiveness of the catheter 10A, since balloon rotation is virtually eliminated, along with the effects of balloon rotation lag.

The alternative embodiment of the catheter 10A further includes a radiopaque spring tip 72A that is positioned distally of the distal end 42A of the balloon member 34A.

The non-over-the-wire catheter 10, 10A of the present invention is relatively uncomplicated and since the distal end 42, 42A of the balloon member 34, 34A is coupled to the core wire 20, 20A via the torsionally soft component 58, 58A, the core wire 20, 20A can be rotated relative to the balloon member 34, 34A with minimal twisting of the balloon member 34, 34A as the catheter 10, 10A is steered through the vascular system of a patient. This reduction in balloon twist permits uniform inflation and deflation of the balloon member 34, 34A which is needed to effectively dilate the stenosis and re-establish acceptable blood flow through the arterial vessel.

Moreover, the non-transmission of torque from the core wire 20, 20A to the balloon member 34, 34A reduces, if not eliminates balloon rotation. Hence, the effects (i.e., dampened steering responsiveness) due to the lag in balloon rotation upon application of torque to the core wire 20, 20A are substantially decreased. The effects of balloon rotation lag are decreased and steering responsiveness improved, because contact between the balloon member 34, 34A and the wall of a guide lumen of a guide catheter and the walls of arterial vessels no longer imparts drag to the distal end 24, 24A of the core wire 20, 20A. This lack of drag alleviates steering difficulties sometimes associated with non-over-the-wire catheters wherein torque is readily transmitted from the core wire to the balloon.

In addition, the torsionally soft component 56, 56A prevents the balloon member 34, 34A and waist tube 26 from being displaced proximally or distally, respectively, along the core wire 20, 20A as the catheter 10 is being maneuvered through a vascular system of a patient.

Although the present invention has been described with reference to preferred embodiments, workers skilled in the art will recognize that changes may be made in form and detail without departing from the spirit and scope of the invention. For example, in considering a preferred commercial embodiment of the catheter of the present invention, it is contemplated that the distal end of the catheter would include a strain relief assembly as disclosed in the commonly assigned application entitled Dilatation Catheter Strain Relief Assembly (Ser. No. 07/852,548) which was filed on even date with this application and which is hereby incorporated herein in its entirety by reference thereto.

What is claimed is:

1. A catheter comprising:
   a tube having a through passage extending from a proximal end to a distal end;
   a guiding member having a proximal end and a distal end, with the guiding member extending distally beyond the distal end of the tube;
   an inflatable balloon member extending around a section of the guiding member and having an interior in fluid communication with the through passage of the tube, the balloon member including a proximal end sealably connected to the distal end of the tube and a distal end; and
   a torsionally soft component coupled between the balloon member and the guiding member, closely adjacent the balloon member, the torsionally soft component absorbing torque which is applied through the guiding member such that the torque is not readily transmitted to the balloon member from the guiding member.

2. The catheter of claim 1 wherein the tube includes:
   an elongate flexible tubular member having an interior passage extending from a proximal end to a distal end; and
   a flexible waist tube having a proximal end and a distal end, the waist tube having its proximal end sealably connected to the tubular member, the waist tube extending distally beyond the distal end of the tubular member about the guiding member to define a distal interior passage in fluid communication with the interior passage of the tubular member.

3. The catheter of claim 1 wherein the torsionally soft component is a torsionally flexible tubular element having a proximal end and a distal end.

4. The catheter of claim 3 wherein the proximal end of the tubular element is secured to the distal end of the balloon member and the distal end of the tubular element is secured to the guiding member, such that the tubular element extends distally beyond the distal end of the balloon member.

5. The catheter of claim 4 wherein the distal end of the balloon member has an inner circumferential surface to which the proximal end of the tubular element is secured.

6. The catheter of claim 4 wherein the proximal and distal ends of the tubular element are secured to the balloon member and guiding member, respectively, by an adhesive material.

7. The catheter of claim 6 wherein the adhesive material is epoxy.

8. The catheter of claim 6 wherein the adhesive material is cyanoacrylate.

9. The catheter of claim 3, and further including:
a flexible, helical coil member having a proximal end and a distal end, the coil member being mounted on the distal end of the guiding member distally of the distal end of the tubular element.

10. The catheter of claim 9, and further including:
a shaping ribbon extending between and connecting the distal end of the coil member to the distal end of the guiding member.

11. The catheter of claim 10 wherein a first fused joint connects the distal end of the coil member to the shaping ribbon, and wherein a second fused joint couples the proximal end of the coil member to the distal end of the guiding member.

12. The catheter of claim 1, and further including:
a substantially rigid inner sleeve coupled between the distal end of the balloon member and the torsionally soft component.

13. The catheter of claim 12 wherein the inner sleeve has a proximal end, a distal end and a through lumen that extends between the proximal and distal ends of the inner sleeve and is configured to freely receive the guiding member, such that the guiding member can rotate relative to the inner sleeve upon the application of torque through the guiding member.

14. The catheter of claim 13 wherein the torsionally soft component is a torsionally flexible tubular element having a proximal end, a distal end and a through opening that extends between the proximal and distal ends of the tubular element, the guiding member extending through the through opening of the tubular element.

15. The catheter of claim 14 wherein the inner sleeve extends proximally from the distal end of the balloon member, wherein the distal end of the tubular element is secured to the proximal end of the inner sleeve and wherein the proximal end of the tubular element is secured to the guiding member, such that the tubular member extends proximally from the proximal end of the inner sleeve.

16. The catheter of claim 15 wherein the proximal and distal ends of the tubular element are secured to the guiding member and inner sleeve member, respectively, by an adhesive material.

17. The catheter of claim 16 wherein the adhesive material is epoxy.

18. The catheter of claim 16 wherein the adhesive material is cyanoacrylate.

19. The catheter of claim 13, and further including:
a flexible, helical coil member having a proximal end and a distal end, the coil member being mounted on the distal end of the guiding member distally of the distal ends of the balloon member and inner sleeve.

20. The catheter of claim 19, and further including:
a shaping ribbon extending between and connecting the distal end of the coil member to the distal end of the guiding member.

21. The catheter of claim 20 wherein a first fused joint connects the distal end of the coil member to the shaping ribbon, and wherein a second fused joint couples the proximal end of the coil member to the distal end of the guiding member.

22. The catheter of claim 1 wherein the tubular member is formed of a super elastic alloy.

23. In a catheter system having a guiding member and an inflatable balloon member extending around a section of the guiding member, the improvement comprising:
a torsionally soft component having a proximal end secured to the balloon member and a distal end secured to the guiding member, such that the tubular member extends distally beyond the distal end of the balloon member, the torsionally soft component absorbing torque which is applied through the guiding member such that the torque is not readily transmitted to the balloon member from the guiding member.

* * * * *